US006320107B1

(12) United States Patent
Nubel

(10) Patent No.: US 6,320,107 B1
(45) Date of Patent: Nov. 20, 2001

(54) SYNTHETIC CORN HYBRID P68

(75) Inventor: Douglas S. Nubel, Bloomington, IL (US)

(73) Assignee: Optimum Quality Grains, LLC, Johnston, IA (US)

( * ) Notice: Subject to any disclaimer, the term of this patent is extended or adjusted under 35 U.S.C. 154(b) by 0 days.

(21) Appl. No.: 09/502,962

(22) Filed: Feb. 11, 2000

(51) Int. Cl.$^7$ ................................ A01H 5/00; A01H 4/00; A01H 1/00; C12H 5/04
(52) U.S. Cl. ................ 800/320.1; 800/298; 800/275; 800/271; 800/268; 800/266; 800/301; 800/302; 800/303; 435/412; 435/424; 435/430; 435/430.1
(58) Field of Search ................ 800/320.1, 298, 800/278, 271, 268, 266; 435/412, 424, 430, 430.1

(56) References Cited

U.S. PATENT DOCUMENTS 5,675,065  10/1997  Bergquist .
5,824,855  10/1998  Bergquist .

Primary Examiner—Gary Benzion
(74) Attorney, Agent, or Firm—Bullwinkel Partners, Ltd.

(57) ABSTRACT

A synthetic hybrid corn plant having the designation P68, produced by crossing two proprietary Optimum Quality Grain, L.L.C. maize synthetics, P41.1B-Lancaster and P58.1wx-Reid. P68 has the unique property of imparting high oil levels in the grain of certain normal and male sterile hybrids when used as a pollinator. P68 is characterized by excellent cold tolerant seedling vigor for rapid emergence in cold soils and excellent early-season adaptability facilitating nicking with early maize hybrids to condition fast dry-down and superior grain quality in the grain arising from the recipient female grain parent. This invention thus relates to the seeds, plants and plant parts of P68, to a tissue culture of P68, to a method of producing P68, to seed corn blends comprising P68, and to a method for producing grain using P68 as a pollinator.

15 Claims, No Drawings

SYNTHETIC CORN HYBRID P68

FIELD OF THE INVENTION

This invention is in the field of plant breeding. Specifically, this invention relates to a novel synthetic corn hybrid having the designation P68 and useful in the proprietary TOPCROSS® grain production system described in U.S. Pat. Nos. 5,704,160 and 5,706,603 by Bergquist et al.

BACKGROUND OF THE INVENTION

Uses of Corn

Corn (*Zea mays* L.) is an important crop used as a human food source, animal feed, and as a raw material in industry. The food uses of corn, in addition to the human consumption of corn kernels, include products of both the dry milling and wet milling industries. The principal products of dry milling include grits, meal and flour. The principal products of wet milling include starch, syrups, and dextrose. A by product of both dry and wet milling is corn oil, which is recovered from corn germ. As an animal feed, corn is used primarily as a feedstock for beef cattle, dairy cattle, swine, poultry, and fish.

Industrial uses of corn mainly consist of the use of corn starch produced by wet milling and corn flour produced by dry milling and the whole kernel fermentation for production of food-grade and industrial use ethanol. The industrial applications of corn starch and flour are based on their functional properties, such as viscosity, film formation ability, adhesiveness, absorbent properties and ability to suspend particles. Corn starch and flour are used in the paper and textile industries and as components in adhesives, building materials, foundry binders, laundry starches, sanitary diapers, seed treatments, explosives, and oil-well muds. Plant parts other than the corn kernels are also used in industry. For example, stalks and husks can be made into paper and wallboard, and corn cobs can be used for fuel and to make charcoal and as a source of furfural.

Principles of Conventional Plant Breeding

Virtually all of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed an $F_1$ single cross hybrid. The resulting kernels from this intermating are then sold as seed to commercial growers who plant the seed and harvest the second generation, or $F_2$ grain, for use on farm or for commercial sale.

The production of a conventional single cross hybrid seed involves controlling the direction of pollination from one inbred to the other to assure the production of predominantly hybrid (cross pollinated) seed. Typically directed pollination is accomplished by interplanting separate rows of female corn plants with male corn plants. The female, i.e. male sterile, corn plants may be produced by genetic mechanisms which render the corn tassel nonfunctional or by detasseling the plants in the field.

The development of corn hybrids requires the development of homozygous inbred lines or uniform synthetic populations of unique heterotic background, the crossing of these lines or synthetic populations, and evaluation of test crosses. Pedigree breeding and recurrent selection breeding programs are two breeding methods used to develop inbred lines and synthetic populations from breeding populations. Breeding programs combine desirable traits from two or more inbred lines or various broad-based sources into breeding pools from which new inbred lines or synthetic populations are developed by inbreeding or random mating and selection of desired phenotypes. The new inbreds and/or synthetic lines are crossed with other inbred lines and/or synthetic populations to produce hybrids. The hybrids from these crosses are evaluated to determine which have commercial value and agronomic usefulness.

Pedigree breeding starts with the crossing of two genotypes, each of which may have one or more desirable characteristics that is lacking in the other or which complements the other. If the two original genotypes do not provide all of the desired characteristics, other sources can be included during the breeding. In the pedigree breeding method, superior plants are selfed or random mated and the resulting seed selected in successive generations. Pedigree records of ancestry are carefully maintained for each family and ear row selection through succeeding generations. In the succeeding generations, the heterozygous condition of the corn germplasm gives way to homozygous true breeding lines as a result of inbreeding and selection. Typically five or more generations of inbreeding and selection is practiced: i.e., $F_1$ to $F_2$; $F_2$ to $F_3$; $F_3$ to $F_4$; $F_4$ to $F_5$, etc.

Backcrossing can be used to improve an inbred line by transferring a specific desirable trait from one inbred or source to another inbred that lacks that trait. This can be accomplished, for example, by first crossing a superior inbred (recurrent parent) to a donor inbred (nonrecurrent parent). The donor inbred carries (donates) the appropriate gene(s) for the desired trait to the next generation. After five or more backcross generations with selection for the desired trait, the inbred will be heterozygous for loci controlling the characteristic being transferred, but will be like the superior parent for most or almost all other genes. The last backcross generation can be selfed to produce a pure breeding progeny for the gene(s) being transferred.

An important consequence of the homozygosity and homogeneity of the inbred lines is that the hybrid between any two inbreds will always be the same. Once the inbreds or synthetics that give the best hybrid have been identified, the hybrid seed can be reproduced indefinitely as long as the homogeneity of the inbred or synthetic parents is maintained.

A synthetic hybrid consists of an array of similar genotypes that were identified from intercross tests and bulked into a random mating population having a desired phenotype. The intercrosses between two different heterotic groups results in the continuous production of a specific synthetic hybrid of desired phenotype.

As previously noted, a single cross hybrid is produced when two unrelated inbred or synthetic lines are crossed to produce the $F_1$ progeny. A three-way cross hybrid is produced from three inbred lines (or synthetics) where two of the inbred lines (or synthetics) are crossed (A×B) and then the resulting $F_1$ hybrid is crossed with the third inbred (or synthetics) (A×B)XC. A double cross hybrid is produced from four inbred lines (or synthetics) by crossing pairs (A×B) and (C×D) and then crossing the two $F_1$ hybrids (A×B)x(C×D).

Much of the hybrid vigor exhibited by $F_1$ hybrids is lost in the next generation ($F_2$). Consequently, seed (grain) from hybrid varieties is not used for planting stock.

The objective of typical plant breeding is to combine in a single variety/hybrid the desirable traits of the parental lines. For field crops such as corn, these desirable traits may include resistance to diseases, insects, herbicide tolerance, and tolerance to heat and drought, reducing time to crop maturity, and improved agronomic quality. With mechanical harvesting of many crops, uniformity of plant characteristics such as germination time and stand establishment, growth rate, and fruit/seed size are also desirable.

The problem with conventional breeding techniques is that there are several grain quality traits, such as high oil content, that cannot readily be combined in a high-yielding single cross hybrid. By contrast, synthetic hybrids, such as the one described herein, when used as a pollinator in the TOPCROSS® grain production system, can impart desirable grain quality characteristics, such as high oil content, to the resulting $F_1$ grain without significant loss in yield.

Synthetic Varieties

Corn has male flowers, located on the tassel, and female flowers, located on the ear, of the same plant. Because of this monoecy, corn plants can be bred by both self-pollination and cross-pollination techniques. Corn is self-pollinated if pollen from one flower is transferred to the same or another flower on the same plant. Corn is cross-pollinated if the pollen comes from a flower on a different plant.

Plants that have been self-pollinated and selected for uniform type over many generations become homozygous at almost all gene loci and produce a uniform population of true breeding progeny. Cross pollination between two homozygous lines produces a uniform population of hybrid plants that nevertheless may be heterozygous for many gene loci. A cross between two plants that are each heterozygous for a number of gene loci will produce a population of hybrid plants that differ genetically and will not be uniform.

Natural pollination occurs when wind blows pollen from tassels to silks that protrude from tops of the incipient ears on plants of the same genotype and different genotype, resulting in both self- and cross-pollination. When a population of genotypes are combined from all possible intercrosses among a number of selected genotypes and are allowed to open pollinate, the result is called a synthetic variety. A synthetic variety is made up of genotypes which previously have been tested for their ability to produce a superior progeny when crossed in all combinations.

Corn plants may be maintained as an outcrossing synthetic population that is much less homogeneous than a self-pollinated group. Every plant in such a group is certain to be heterozygous at many or most loci, and this heterozygosity must either be maintained during a breeding program or restored at the end of the program, if productivity is to be satisfactory. The main requirement in maintaining a synthetic line is that a sufficient number of plants of heterozygous background be maintained to recover the gene frequencies that are desired for the synthetic population so as to prevent genetic drift toward undesired gene frequencies.

The Desirability of High Oil Content Grain

The concentration of oil in most varieties of corn ranges from less than 3.0 percent to 4.5 percent at 0% moisture. Embryos of ordinary corn can contain 30 percent oil, while embryos of high oil corn strains can contain as much as 50 percent oil and are much larger in size than ordinary corn embryos.

There are several reasons for wanting to develop a method for growing corn that is high in oil content. First, corn oil is a premium oil and regularly more valuable than starch, the other major component of corn kernels. Second, high oil corn possesses a higher available energy content than ordinary corn, and thus is a more valuable feed for poultry and livestock. In animal feeding trials it has been found that less high oil corn is required per unit of gain than is required with ordinary corn. In addition, high oil corn requires substantially less soybean meal to balance a typical animal diet, and may be used to replace oil containing additives in animal feed.

Additional impetus was given to breeding corn for high oil by the development of wide-line nuclear magnetic resonance spectroscopy (NMR) and near-infrared spectroscopy (NIR) as analytical tools for the nondestructive analysis of bulk or single kernel samples that can be carried out in as little as two seconds. The development of such tools made it much easier and much quicker to determine the oil content of grain, thereby encouraging experimentation in the area of breeding for high oil.

Thus there exists at present a growing market for corn having high oil, increased protein and other special end-use properties which is not met by corn of standard composition. The diverse types of corn available to plant breeders provides a potential for modification of quality and quantity of grain protein, starch, and oil. Corn now can be developed to more precisely meet the specific nutritional requirements of animals or to meet particular industrial needs.

The TOPCROSS® Grain Production System

Unfortunately, high oil is a property that cannot readily be achieved in a high yielding single-cross hybrid. This is because oil content, while being a moderately heritable trait, is influenced by a series of oil genes that have additive effects on oil content and occur at a complex of loci in at least eight linkage groups that influence the amount of oil in the grain of the progeny. Obtaining a high yielding single cross hybrid having all or most of these oil genes can take many years of breeding. Further increasing the difficulty of breeding for high oil content is the fact that the grain yield of higher oil hybrids is generally inferior when compared to elite dent corn hybrids.

A method of producing a high yield of corn having high oil content without requiring years of breeding is described in Bergquist et al. U.S. Pat. No. 5,704,160. The primary aspect of this method, known as the TOPCROSS® grain production system, is the interplanting of a pollinator corn plant possessing the characteristics for significantly increasing oil and protein levels in the resulting grain with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Need for Superior Pollinators

Critical to the success of the TOPCROSS® grain production system is the use of a pollinator capable of enhancing the grain quality traits of the $F_1$ offspring. To obtain such pollinators, the corn breeder must select and develop corn plants that have the traits that result in superior inbred and synthetic parental lines.

The pollinator for the TOPCROSS® grain production system need not be genetically homozygous (inbred) or even uniform in appearance, and need not be selected for genetic combining ability with female plants. However, the pollinator should have uniform desirable grain quality characteristics, such as high oil, that will influence the grain quality characteristics of the $F_1$ offspring, and the ability to pollinate the female plants. A hybrid obtained by crossing two synthetic populations of different heterotic backgrounds results in a synthetic hybrid with predictable heterozygosity and genetic variability among plants that is particularly useful as a male pollinator in blends with male sterile hybrid grain parents for use in the TOPCROSS® grain production system. Some genetic variability is desirable because it extends the flowering period of the pollinator. P68 was developed to achieve these characteristics.

Advantages of Synthetic Hybrids

The use of synthetic hybrids (such as P68) as TOPCROSS® grain production system pollinators affords a number of advantages over the use of inbreds, hybrids produced from single crosses, or hybrids produced from three way crosses. For instance, synthetic hybrids can be developed more rapidly than commercial hybrids. Specifically, the use of a synthetic population can more rapidly establish stability of dominant oil genes, thus by-passing the many generations of inbreeding that is required to produce inbreds for making single cross hybrids.

Second, synthetic hybrids often have excellent vigor comparable to that of commercial hybrids. Inbreds, by contrast, typically lose vigor with each successive generation of inbreeding. This is an important advantage of synthetics because pollinator vigor is critical for ample pollen shed at the time of silking in the TOPCROSS® grain production system. Synthetic hybrid P68 expresses cold vigor in seedling growth stages greater than even most open pollinated synthetic populations.

Third, a synthetic variety, utilizing heterosis in which pollination control is a factor, is more likely to disperse pollen over a longer period of time than a single cross hybrid. The predictable greater variability of synthetic varieties as compared with single crosses permits more flexibility to meet the changing growing conditions typical of field production. In addition, because of the longer flowering period, fewer synthetic pollinators need be developed to be used in blends with many different grain parents.

Fourth, the synthetic hybrid pollinator is more easily produced during periods of heat and drought stress on dryland production than a single-cross hybrid using less vigorous inbred seed stocks. For example, in Applicant's non-irrigated dryland field tests conducted during 1993 and 1994, production of synthetic hybrid seed remained relatively constant at about 55 bushels per acre despite the fact that rainfall accumulation during the critical months of May, June and July fell from 40.84 cm in 1993 to 13.82 cm in 1994. Over the same period, single cross seed production in Applicant's test fields using inbred seed stocks fell to less than 25 bushels per acre in 1994 from 55 bushels per acre in 1993.

Fifth, the single cross synthetic hybrid pollinator which results from the cross of two parental synthetic populations, A×B, is more quickly produced in a single generation compared to a three-way cross pollinator (A×B)C that requires an additional plant generation to produce the hybrid three-way cross pollinator. For example, the A×B synthetic hybrid is simply produced in a single plant growing generation in the production of P68 single-cross synthetic hybrid while the three-way cross synthetic hybrid pollinator would require an additional plant generation to produce the final hybrid (A×B) crossed to the parental C-population to produce a synthetic three-way hybrid cross designated (A×B)C.

SUMMARY

According to the invention, there is provided a novel synthetic corn hybrid, designated P68, that when used to pollinate an elite male sterile hybrid grain parent, produces commercial grain exhibiting improved quality grain traits, including high oil and protein. Furthermore, when P68 is used to pollinate male sterile hybrid grain parents that are harvested as whole plants at approximately 50 percent plant moisture, it produces commercial fodder that expresses improved feeding quality traits, including improved feed efficiency and rate of weight gain.

P68 is characterized by excellent cold tolerant seedling vigor for rapid emergence in cold soils and excellent early-season adaptability facilitating nicking with early maize hybrids to condition fast dry-down and superior grain quality in the grain arising from the recipient female grain parent.

The invention thus relates to the seeds, plants and plant parts of P68, to a tissue culture of P68, to a method of producing P68 from P41.1B and P58.1wx synthetic populations, to seed corn blends comprising P68, and to a method for producing grain using P68 as a pollinator.

Definitions

In the description and examples that follow, a number of terms are used. In order to provide a clear and consistent understanding of the specification and claims, including the scope to be given such terms, the following definitions are provided:

Backcross. The cross of a hybrid to either one of its parents. The offspring of such a cross is referred to as the backcross generation.

Backcross Method of Breeding. A system of breeding carried out by several generations of backcrossing to one of the parents of a hybrid and subsequent selection. The characteristics of the recurrent parent are retained for the most part, and characteristics from the nonrecurrent parent are added.

Bulk Method of Breeding. The growing of segregating generations of a hybrid of self-pollinating crops in a bulk, with or without mass selection, followed by individual plant selection in $F_6$ or later generations.

Cytoplasmic Inheritance. Transmission of hereditary characters through the cytoplasm as distinct from transmission by genes carried by chromosomes. Detected by differing contribution of male and female parents in reciprocal crosses.

Diallel Cross. The crossing of all possible combinations of a series of genotypes.

Donor Parent. The parent from which one or a few genes are transferred to the recurrent parent in backcross breeding.

Ear Height. The ear height is a measure from the ground to the top developed ear node attachment and is measured in centimeters.

Elite. This term characterizes a plant or variety possessing favorable traits, such as, but not limited to, high yield, good grain quality and disease resistance.

Embryo. The rudimentary plant in a seed. The embryo arises from the zygote. In high oil corn breeding, increases in oil content are accompanied by increases in embryo size.

Endosperm. The nutritive tissue formed within the embryo sac in seed plants. It commonly arises following the fertilization of the two primary endosperm nuclei of the embryo sac by the two male sperms. In a diploid organism the endosperm is triploid.

Express. To manifest a genetic character trait.

$F_1$. The first generation of a cross.

$F_2$. The second filial generation obtained by self-fertilization or crossing inter se of $F_1$ individuals. Subsequent generations are $F_3$, $F_4$, $F_5$, etc.

GDD Shed. The number of growing degree days or heat units required for an inbred line or hybrid to reach anthesis or pollen shed from the time of planting. Growing degree days are calculated by the Barger Method, where the heat units for a 24-hour period are:

$$GDD = \frac{(Max.\ Temp. + Min.\ Temp.)}{2} - 50.$$

The highest maximum temperature used is 86 degrees F. and the lowest minimum temperature used is 50 degrees F. For each hybrid it takes a certain number of GDDs to reach various stages of plant development. GDDs are a way of measuring plant maturity.

Genotype. The fundamental genetic constitution of an organism.

Germ. The embryo of the corn kernel. It contains most of the oil found in the kernel.

Grain. Mature corn kernels produced by commercial growers for purposes other than growing or reproducing the species.

Grain Parent. Male sterile, elite hybrid that comprises a large majority of the plants in the TOPCROSS® grain production system.

Grain Parent Seed. Corn seed used to produce grain parent plants.

Grain Quality. The general quality of shelled grain as it is harvested based on the color of the harvested grain, any mold on the grain, and any cracked grain.

Grain Quality Trait. Any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Heterozygous. A genetic condition existing when different alleles reside at corresponding loci on homologous chromosomes.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes.

Hybrid Vigor. The phenomenon in which the cross of two stocks produce hybrids that show increased vigor-heterosis compared to the parent stocks.

Inbred. A substantially homozygous individual, variety or line.

Inbred Line. (1) A line produced by continued inbreeding. In plant breeding a nearly homozygous line usually originating by continued self-fertilization, accompanied by selection. (2) A relatively homozygous line produced by inbreeding and selection.

Kernel. The corn caryopsis comprising a mature embryo and endosperm which are products of double fertilization.

Line. (1) A group of individuals from a common ancestry. (2) A narrowly defined group that is a variety.

Male Sterility. A condition in which pollen is substantially absent or non-functional in flowering plants.

Moisture. The actual percentage of moisture of the grain at harvest.

Pedigree. A record of the ancestry of an individual, family, or strain.

Pedigree Breeding. A system of breeding in which individual plants are selected in the segregating generations from a cross on the basis of their desirability and on the basis of a pedigree record.

Percent Oil. The oil concentration of a corn kernel expressed on a dry weight basis.

Percent Yield. The yield obtained for a hybrid in terms of percent of the mean for the experiments in which it was grown.

Phenotype. (1) The physical or external appearance of an organism as contrasted with its genetic constitution (=genotype). (2) A group of organisms with similar physical or external makeup. (3) The observed character of an individual without reference to its genetic nature.

Plant Height. This is a measure of the height of the hybrid from the ground to the tip of the tassel and is measured in centimeters. The data is given in percentage of mean of the experiments in which the hybrid was grown.

Pollen Grain. A microspore in flowering plants that germinates to form the male gametophyte which contains three haploid nuclei. One of these fertilizes the ovum, a second fuses with the two polar nuclei to form the triploid endosperm, and the third degenerates once double fertilization has been accomplished.

Pollinators. Male fertile corn plants used to pollinate male sterile hybrid corn plants in order to produce a Grain Quality Trait in the resulting F1 grain.

Population. In genetics, a community of individuals which share a common gene pool.

Seed. Mature corn kernels produced for the purpose of propagating the species.

Single Cross. A cross between two different genotypes, each of which may be an inbred or synthetic.

Synthetic (Population). A genetically heterogeneous collection of plants of known ancestry created by the intermating of any combination of inbreds, hybrids, varieties, populations, races or other synthetics.

Synthetic Hybrid. A hybrid in which one or more genotypes used to make the hybrid is a synthetic.

TC BLEND®. A registered trademark of E.I. du Pont de Nemours and Company for a physical mixture of two or more types of seed utilized in the TOPCROSS® Grain Production System.

Test Weight. The measure of the weight of the grain in pounds for a bushel volume.

TOPCROSS®. A registered trademark of E.I. du Pont de Nemours and Company for the TOPCROSS® Grain Production System.

Yield (Bushels/Acre). The yield of corn in bushels/acre is the number of bushels of grain at harvest per acre, where one bushel is equal to 56 pounds adjusted to 15.5% moisture.

DETAILED DESCRIPTION OF THE INVENTION

P68 is a yellow dent corn, high oil single cross synthetic hybrid having superior agronomic characteristics and the ability to impart desirable grain quality traits to a first generation grain when used as a pollinator in the TOPCROSS® grain production system.

Synthetic hybrid P68 is produced by planting synthetic populations P41.1B and P58.1wx, allowing one synthetic to pollinate the other, and harvesting the resulting seed. Either synthetic parental population may be used as female parent or male parent. Preferably, synthetic P41.1B is the female of the cross and synthetic P58.1wx is the male of the cross because of the larger seed size grade-out resulting from the P41.1B seed parent in hybrid synthetic production. Production planting of the male and female synthetics can be made at the same time due to the fact that male pollen is shed at the same time the female silks are receptive to the pollen.

P41.1B and P58.1wx were produced by conducting a series of crosses, selfings and backcrosses beginning with the crossing of LH51 with ASKC28 (for P41.1B) and the selection of early plant segregants of waxy phenotype from ASKC28 (for P58.1wx). During the random mating generation of development of P41.1B and P58.1wx, test crosses were made to a hybrid grain parent tester and the resulting grain was analyzed to identify normal grain type segregants with favorable dominant oil genes expressing high oil in the genetic segregants.

When produced according to the method disclosed herein, both P41.1B and P58.1wx breed true, that is, produce a P68 synthetic hybrid that is both reproducible and usable as a high oil pollinator.

Characteristics of P68

Synthetic corn hybrid P68 most closely resembles maize synthetics ASKC28, ASKC20 and UHO in characteristics of plant type, ear type, kernel type and usage, but P68 is considerably earlier in maturity and expresses moderately higher grain test weight with normal grain and dent phenotype that expresses a moderately soft starch.

P68 synthetic hybrid has the following characteristics, based on data primarily collected at the Applicant's El Paso, Ill. research facility (numerical values given are averages taken across a fifty plant sample):

TABLE 1

SYNTHETIC HYBRID P68 DESCRIPTION INFORMATION

| | |
|---|---|
| Type: | Dent/High Oil Most Northern, Central, and Northeastern Regions of USA Cornbelt |
| Region Best Adapted: | Zones 1-2-3 |

A. Maturity:

| | |
|---|---|
| Synthetic Maize Hybrid: | P68 |
| Heat Units from Emergence to Shed: | 1019 GDD (1998) |
| Heat Units from Emergence to Silk: | 1058 GDD (1998) |
| Heat Units from 50% Silk to 25% Kernel Moisture: | 1403 GDD (1998) |
| Heat Units from Emergence to 25% Kernel Moisture: | 2463 GDD (1998) |
| No. Reps.: | 8 |

B. Plant Characteristics:

| | |
|---|---|
| Height (to tassel tip): | 215 cm |
| Length of Top Ear Internode: | 14 cm |
| Number of Ears per Stalk: | Slight two-ear tendency |
| Ear Height (to base of top ear): | 32 cm |
| Number of Tillers: | Mostly none, occasional one |
| Cytoplasm Type: | Normal |
| Brace Root Color: | Green with few purple |
| Number of Brace Root Nodes: | Slight two-node tendency |
| Number of Brace Roots: | 13 |
| Stalk: | Straight |

TABLE 1-continued

SYNTHETIC HYBRID P68 DESCRIPTION INFORMATION

| | |
|---|---|
| Type: | Dent/High Oil Most Northern, Central, and Northeastern Regions of USA Cornbelt |
| Region Best Adapted: | Zones 1-2-3 |

C. Leaf:

| | |
|---|---|
| Color: | Green |
| Stalk Color: | Green |
| Angle from Stalk: | 54 Degrees |
| Attitude of Blade: | Slightly curved |
| Marginal Waves (number): | 2–3, few |
| Number of Leaves (mature plants): | 11 |
| Sheath Pubescence: | Smooth, segregating for smooth and pubescence |
| Color of Sheath: | Pale green |
| Longitudinal Creases: | Absent |
| Length (Ear node leaf): | 74 cm |
| Width (widest point, ear node leaf): | 10 cm |
| Coleoptile Sheath Color: | Mostly green with a few purple |
| First Leaf, Shape of Tip | Round |

D. Tassel:

| | |
|---|---|
| Attitude of Lateral Branches: | Mostly straight, segregating recurved |
| Number Lateral Branches: | 14 |
| Length of Lateral Branches: | 16 cm |
| Branch Angle from Central Spike: | 57 degrees |
| Length of Main Axis Above Lowest Branch: | 38 cm |
| Length (from flag leaf): | 49 cm |
| Peduncle Length (flag leaf to basal branches): | 10 cm |
| Anther Color: | Yellow |
| Glume Color: | Green |
| Density of Spikelets: | Medium |

E. Ear (Husked Ear Data Except When Stated Otherwise)

| | |
|---|---|
| Length: | 17 cm |
| Weight (dried to 15.5% grain moisture): | 151 gm |
| Mid-point Diameter: | 4 cm |
| Silk Color (at silking): | Pale green |
| Husk Extension (Harvest stage): | Short, 7 cm (ear tip occasionally exposed) |
| Husk Leaf (number): | 6 |
| Husk Leaf Length: | 5 cm |
| Number of Husks: | 12 |
| Taper of Ear: | Average taper |
| Position at Dry Husk Stage: | Upright |
| Kernel Rows: | 16; Distinct, straight |
| Husk Color (fresh): | Light green |
| Husk Color (dry): | Buff |
| Shank Length: | 21 cm long |
| Shank (No. of internodes): | 10 |
| Drying Time (unhusked ear): | Average |
| Husk Length: | 31 cm |
| Husk Width: | 17 cm |
| Husk Area: | 529 cm$^2$ |

F. Kernel (dried, size from ear mid-point):

| | |
|---|---|
| Length: | 11 mm |
| Width: | 7 mm |
| Thickness: | 4 mm |
| Shape Grade (% rounds): | 25% (±3%) based on parent test |
| Pericarp Color: | Colorless |
| Aleurone Color: | Homozygous; yellow |
| Cap Color: | Yellow |
| Endosperm Color: | Yellow |
| Endosperm Starch Type: | Normal starch, segregating for soft starch |
| Gm Wt/100 Seeds (unsized): | 22 gm |

TABLE 1-continued

SYNTHETIC HYBRID P68 DESCRIPTION INFORMATION

| | |
|---|---|
| Type: | Dent/High Oil<br>Most Northern, Central, and Northeastern Regions of USA Cornbelt |
| Region Best Adapted: | Zones 1-2-3 |
| Test Weight: | 57 lbs./bu. |
| Percent Oil: | 19.64 percent (1998) |
| Percent Protein: | 14.0 percent (1998) |
| Percent Starch: | 47 percent (1998) |
| Density: | 1.18 gm/ml (1998) |
| G. Cob (dried, size from ear mid-point): | |
| Diameter at mid-point: | 25 mm |
| Strength: | Strong |
| Color: | Red, segregating for white and red cob color but was heterozygous for red. |
| H. Diseases: | |
| Northern Leaf Blight: | Intermediate |
| Goss's Bacterial Wilt: | Intermediate |
| Southern Corn Leaf Blight: | Susceptible |
| Heat Smut: | Susceptible |
| Common Smut: | Resistant |
| Stewart's Bacterial Wilt: | Intermediate |
| Corn Lethal Necrosis: | Susceptible |
| Northern Leaf Spot: | Intermediate |
| Common Northern Rust: | Intermediate |
| Southern Rust: | Susceptible |
| Eye Spot: | Intermediate |
| Gray Leaf Spot: | Susceptible |
| Fusarium Ear Rot: | Resistant |
| Fusarium Stalk Rot: | Intermediate |
| Diplodia Ear Rot: | Susceptible |
| Diplodia Stalk Rot: | Intermediate |
| MDMV: | Susceptible |
| Stunt: | Susceptible |
| Stay Green: | Intermediate |
| I. Insects: | |
| European Corn Borer: | Susceptible |
| J. Variety most closely resembling P68: | |
| Character | Synthetic Hybrid, Hybrid, and/or Inbred |
| Maturity | P53, P39, Pfister Hybrid 2020 |
| Plant Type | ASKC28, UHO, ASKC20, P39, P53 |
| Ear Type | ASKC28, UHO, ASKC20, P39, P53 |
| Kernel Type | UHO, ASKC20, ASKC28 |
| Usage | ASKC28, UHO, ASKC20 |

P68 is adapted over a wide area of the northern corn belt and can be used advantageously as a pollinator in seed blends with male sterile hybrids from approximately 95–100 relative maturity based on the Minnesota Relative Maturity Rating System for harvest moisture of the grain. P68 cold test vigor was excellent in laboratory tests, exhibiting 95 percent emergence compared to 90 percent emergence for ASKC20, 91 percent emergence for UHOC3, and 83 percent emergence for ASKC28. Kernel size-out is also very good for P68, with approximately 75 percent of the kernels falling in the medium flat category.

Although P68's primary use would be as a pollinator in the TOPCROSS® grain production system with blends of early maturing corn hybrid male sterile grain parents, P68 is also an acceptable male to be crossed to later maturing full season high oil pollinators to develop medium maturity pollinators for expanding the use of its genetics to fuller season maturity grain parents.

Pollen production is good with P68. Under extreme heat and drought stress, P68 may top fire and have some tassel blasting (necrosis of top leaves and tassel, respectively). P68 sheds pollen for approximately nineteen days (Table 3) and should be blended in sufficient concentrations (at approximately ten percent pollinator seed to ninety percent male sterile hybrid grain parent seed) to ensure adequate pollen in commercial production of high oil corn grain where it is used as a male pollinator.

As a pollinator, P68 has shown uniformity and stability within the limits of environmental influence for the grain traits of yield, moisture, oil concentration and protein concentration as shown in Tables 2–4. P68 has expressed segregation for red and white cob color because of the genetic differences of P41.1B and P58.1wx synthetic parental populations. P68 is a synthetic hybrid that has been maintained by hand and cross pollination in isolated fields with continued observation of high oil for uniformity of dominant high oil genetics. Although segregating for cob color, glume color and plant height in test crosses, P68 synthetic has consistently expressed high oil across different environments.

P68 is an early maturity flowering synthetic hybrid, broadly adapted to the corn growing areas of the Northern United States and Southern Canada. P68 has expressed high oil and excellent cold soil seedling vigor that conditions low grain moisture in the grain of male sterile hybrid grain parents.

Benefits of P68 as a Pollinator

In field tests of the TOPCROSS® grain production system using P68 as the pollinator and a male sterile hybrid grain parent, P68 was found to induce superior grain quality characteristics in grain arising on the male sterile hybrid. That is to say, the superior grain quality traits and high oil characteristics of P68 were transferred to the grain of the male sterile hybrid grain parent.

In field tests, P68 and male sterile grain parent plants were allowed to grow unmolested to maturity. Both varieties were allowed to continue to grow and natural cross-pollination was allowed to occur by the action of the wind as is normal with most grasses, including corn. Of course, only pollen from the fertile male parent, P68, was available for pollination of the male sterile hybrid grain parent; the tassels, or flower bearing parts, of the grain parent having been rendered sterile by genetic/cytoplasmic mechanisms. For convenience, the grain harvested from the male sterile grain parent plants and the P68 plants will hereinafter be referred to as "high oil corn grain."

The fields where high oil corn grain was produced were well isolated from other corn fields to prevent any accidental contamination with ambient pollen. Such isolation techniques may be accomplished by a timed delay with other hybrid corn production fields or by using a space distance pattern of more than 70 m from normal corn, a technique well known to those skilled in the art of the seed corn industry.

Both the male fertile pollinator and male sterile hybrid grain parent varieties comprising the corn seed blend were allowed to continue to grow and be harvested. The ears harvested from the male sterile grain parent expressed the higher grain yield potential of the elite male sterile grain parent and the high oil, protein and grain density qualities of the pollen parent. The grain from the male parent synthetic variety ears may be harvested along with the grain of the male sterile grain parent hybrid for high oil corn use.

Because the same oil source (i.e. ASKC28) was used in the development of the P41.1B-Lancaster and P58.1wx-Reid parental populations, only modest heterotic effects for yield were expressed in P68. The low grain yields expected from synthetic hybrid P68 pollinator dictated the need for a low percent of pollinator in the pollinator-grain parent seed blend so as to maximize yield, but a high enough percent was needed to ensure sufficient pollination of the elite male sterile grain parent hybrid.

EXAMPLES OF USING P68 AS A POLLINATOR

In the examples that follow, the characteristics of high oil corn grain produced using P68 as a pollinator are provided.

1998 Strip Test Trials

First year (1998) strip tests trials were conducted at El Paso, Ill. comparing the characteristics of grain from various hybrids rendered male sterile and pollinated by P68 with characteristics of grain produced from grow outs of the same hybrids in their fertile state ("Hybrid Self"). The hybrids used were Pioneer Hybrid P37M81 and Pfister Hybrids 2020, 2025, 3034, 1400 and 1571. The results are presented in Table 2.

"Oil Percent", expressed as a percentage of the total kernel dry weight for both grain produced from the pollination of the male sterile hybrid by P68 and for the grow out of the fertile hybrid. Thus oil percent is a measure of the content of oil in grain at harvest. Oil percent was determined by NIR on a dry matter basis (0 percent moisture).

"Protein Percent", expressed as a percentage of protein in the grain on a dry matter basis as determined by NIR for both grain produced from the pollination of the male sterile hybrid by P68 and for the grow out of the fertile hybrid.

"Test Weight", expressed as the weight of the grain in pounds for a given volume (bushel) adjusted for percent moisture for both grain produced from the pollination of the male sterile hybrid by P68 and for the grow out of the fertile hybrid.

Grain yield, moisture percent, oil percent, protein percent and test weight for the grain produced by the male sterile/P68 blends are also expressed as a percent of the same traits from the fertile grain parent grow outs (% of GP)

Grain Yield Comparisons—High Oil Corn Grain Versus Hybrid Self

In the 1998 first year strip test trials (Table 2), blends of 8–9 percent pollinator seed and 91–92 percent male sterile hybrid seed were planted and grown to maturity. Grain from both the male sterile hybrid plants and the pollinator plants (i.e., high oil corn grain) was harvested.

As shown in Table 2, the overall mean yield of grain produced by the pollination of the male sterile hybrids by P68 during the first year (1998) strip tests was 83 percent of

TABLE 2

1998 P68 Strip Tests Results - El Paso, Illinois

| Hybrid Grain Parent | Grain Yield (Bu/A.) | | | Moisture Percent | | | Oil Percent | | | Protein Percent | | | Test Weight (Lbs./Bu.) | | |
|---|---|---|---|---|---|---|---|---|---|---|---|---|---|---|---|
| | Top-Cross | % of GP | Hybrid GP Self | Top-Cross | % of GP | Hybrid GP Self | Top-Cross | % of GP | Hybrid GP Self | Top-Cross | % of GP | Hybrid GP Self | Top-Cross | % of GP | Hybrid GP Self |
| Pioneer P37M81-Sdms | 125.3 | 81 | 155.0 | 14.9 | 110 | 13.6 | 8.16 | 183 | 4.45 | 8.5 | 87 | 9.8 | 54.8 | 97 | 56.6 |
| Pfister 2020-Sdms | 125.3 | 84 | 148.6 | 20.7 | 138 | 15.0 | 8.64 | 192 | 4.51 | 8.1 | 93 | 8.7 | 52.2 | 92 | 56.8 |
| Pfister 2025-Sdms | 144.2 | 85 | 170.3 | 19.1 | 137 | 13.9 | 6.62 | 189 | 3.50 | 8.1 | 94 | 8.6 | 53.3 | 93 | 57.0 |
| Pfister 3034-Sdms | 130.6 | 88 | 147.6 | 22.6 | 112 | 20.1 | 9.04 | 204 | 4.44 | 8.0 | 99 | 8.1 | 51.7 | 92 | 56.3 |
| Pfister 1400-Sdms | 105.1 | 72 | 146.1 | 15.4 | 108 | 14.2 | 7.59 | 164 | 4.63 | 8.4 | 91 | 9.2 | 56.1 | 94 | 60.0 |
| Pfister 1571-Sdms | 128.0 | 89 | 143.5 | 19.0 | 131 | 14.5 | 8.19 | 166 | 4.92 | 8.5 | 89 | 9.5 | 55.1 | 95 | 58.0 |
| Overall Mean | 126.7 | 83 | 151.9 | 18.6 | 122 | 15.2 | 8.04 | 182 | 4.41 | 8.3 | 93 | 8.9 | 54.0 | 94 | 57.5 |

Traits obtained from the strip test include the following:

"Grain yield", expressed in bushels per acre for both the grain produced by the pollination of the male sterile grain parent hybrid by P68 and the grain produced from the grow out of the fertile hybrid.

"Moisture Percent", expressed as a percentage of total kernel weight for both grain produced from the pollination of the male sterile hybrid by P68 and for the grow out of the fertile hybrid. Moisture percent was determined by distillation on a Brown-Duvel moisture tester manufactured by the Seed Trade Reporting Bureau of Chicago, Ill. Electronic moisture testers were calibrated against the moisture determinations of the Brown-Duvel moisture tester in field harvest tests.

the overall mean yield of grain produced from the fertile grain parent grow outs in six comparisons.

Moisture Comparisons—High Oil Corn Grain Versus Hybrid Self

Conventional high oil hybrids traditionally express higher grain moisture at harvest and are slower to dry down than lower-oil dent hybrids of the same maturity. To test this concept of higher moisture associated with higher oil content of grain, comparisons were made of moisture at harvest of grain resulting from the pollination by P68 of the male sterile hybrids and grain resulting from the self pollination of the comparable fertile hybrids.

In the first year (1998) trials (Table 2), the overall mean grain moisture at harvest from the sterile grain parent hybrids pollinated by P68 was higher than the grain moisture from the fertile grain parent hybrids alone in the hybrid grain parent comparisons. Since higher oil content resulted in higher significant moisture differences in these comparisons, the first year data did support the conventional theory regarding the relationship between oil content and grain moisture.

Oil Comparisons—High Oil Corn Grain Versus Hybrid Self

In the first year (1998) strip tests made at El Paso, Ill. the oil contents of grain produced from the pollination by P68 of the male sterile hybrids were compared to grain produced from the self pollination of the comparable fertile hybrids. The results, shown in Table 2, show a consistent increase in oil percent in the high oil corn grain compared to the hybrid selfs. To take but two examples, there was about a 204 percent increase in oil when Pfister Hybrid 3034-Sdms was pollinated by P68 (9.04% versus 4.44%), and about a 192 percent increase in oil when Pfister Hybrid 2020-Sdms was pollinated by P68 (8.64% versus 4.51%).

Protein Comparisons—High Oil Corn Grain Versus Hybrid Self

In first year (1998) strip tests (Table 2), protein content of the grain resulting from the pollination of the male sterile hybrid by P68 was compared to the protein content of grain produced from open pollinated fertile hybrid checks. Analysis of population means indicated that P68 did not significantly increase protein in the high oil corn grain compared to the grain from the fertile grain parent check. For example, the mean protein level in grain produced by the pollination of Pioneer P37M81-Sdms by P68 was 1.3 percent lower in absolute terms than the protein level in grain produced by the self pollination of fertile P37M81 (8.5% compared to 9.8%).

Test Weight Comparisons—High Oil Corn Grain Versus Hybrid Self

Test weight of grain is a function of kernel density. In first year strip tests, comparisons were made of the test weight of high oil corn grain resulting from the pollination by P68 of male sterile hybrids against the test weight of grain resulting from the self pollination of the comparable fertile hybrids. As shown in Table 2, the overall mean test weight of high oil corn grain was 54.0 Lbs./Bu., or 94 percent of the mean test weight of the selfed hybrids (57.5 Lbs./Bu.).

P68 conditions a slight loss in test weight in the high oil corn grain which is reflected in a slight yield penalty. This is because P68 was developed by crossing P58.1wx, a soft starch phenotype, with P41.1B-Lancaster, a normal starch phenotype. This cross yields a heterogeneous condition in the P68 pollinator, i.e., the presence of two types of male pollen gametes—soft starch and normal starch. When P68 is used as a high oil corn pollinator, the two types of male pollen gametes fertilize the male sterile hybrid grain parent. As a result, some of the high oil corn grain expresses lower test weight (female ovules fertilized by male gametes with soft starch phenotype) and the remainder of the grain expresses normal test weight (female ovules fertilized by male gametes with normal starch phenotype). Overall, the grain exhibits a mid-parent mean that results in a slight loss in test weight which is reflected in a slight yield penalty.

Tassel-Silk Synchronization—P68 Pollen Shed and Grain Parent Silk Extrusion

The success of the TOPCROSS® grain production system is dependent on the synchronization of pollen shed from the pollinator with the extrusion of silks from the male sterile grain parent hybrid, which is termed nicking.

Table 3 presents results of tassel-silk date observations and growing degree days (GDD) to tassel shed and silk flowering for P68 pollinator and Pfister Hybrid 2020, respectively. As shown in the table, in 1998 strip tests the pollination period of P68 began July 5 and ended July 23, a nineteen (19) day period. Peak pollination, i.e., the date during which 50% pollen shedding was achieved, occurred on July 11 which resulted from an accumulation of 1019 GDD from seedling emergence. By comparison, the peak silk extrusion date for Pfister Hybrid 2020 was also July 11. These data indicate that the nicking of pollinator P68 with male sterile Pfister Hybrid 2020 is acceptable for commercial high oil corn grain production.

TABLE 3

Comparison of the Tassel Shedding Period for P68
with the Silk Extrusion Period for Pfister Hybrid 2020
Total Plants Observed - 121
1998 Field Test Data

| Date | July 5 | July 6 | July 7 | July 8 | July 9 | July 10 | July 11 | July 12 | July 13 | July 14 |
|---|---|---|---|---|---|---|---|---|---|---|
| Percent of Pollinator P68 to Start Shedding | 1 | | 7 | 2 | 26 | 20 | 17 | 2 | 11 | 2 |
| Percent of Pollinator P68 to Stop Shedding | | | | | | | | | 1 | 2 |
| Percent of Hybrid 2020 to Begin Silk Extrusion | | | 3 | 7 | 8 | 8 | 9 | 12 | 19 | 7 |
| Growing Degree Days | 881 | 905 | 929 | 953 | 977 | 1000 | 1019 | 1036 | 1058 | 1082 |

| Date | July 15 | July 16 | July 17 | July 18 | July 19 | July 20 | July 21 | July 22 | July 23 |
|---|---|---|---|---|---|---|---|---|---|
| Percent of Pollinator P68 to Start Shedding | 5 | 1 | 3 | 1 | 1 | 1 | | | |
| Percent of Pollinator P68 to Stop Shedding | 10 | 22 | 34 | 7 | 10 | 7 | 3 | 2 | 2 |

TABLE 3-continued

Comparison of the Tassel Shedding Period for P68
with the Silk Extrusion Period for Pfister Hybrid 2020
Total Plants Observed - 121
1998 Field Test Data

| Percent of Hybrid X571-wx to Begin Silk Extrusion | 11 | 5 | 3 | 2 | 2 | 2 | 1 | 1 |
|---|---|---|---|---|---|---|---|---|
| Growing Degree Days | 1103 | 1128 | 1150 | 1174 | 1202 | 1226 | 1255 | 1276 | 1297 |

Comparisons of Oil, Protein and Moisture in Grain Produced from Hybrids Pollinated by P68 and Self Pollinated Fertile Hybrids Harvested Over Time Table 4 presents the oil content, protein content and moisture of grain produced from Pfister Hybrids 2020 and 2020-Sdms-Sib (columns one and two), grain produced from Pfister Hybrids 2020 and 2020-Sdms pollinated by P68 (columns three and four), and grain produced from self-pollinated P68 (column five) when the grain was harvested 36 days after flowering and then harvested on selected days to and beyond the onset of physiological maturity (i.e., black-layer).

Pfister Hybrid 2020-Sdms pollinated by P68 (column 4) expressed 8.4 percent oil content of the grain as early as 761.5 GDD after flowering (August 17), thus indicating a very high level of oil while the plant foliage was green and actively growing. This permits an early harvest for silage and/or earlage while maintaining a high energy recovery from the grain.

A comparison of the protein content data for Pfister Hybrid 2020-Sdms pollinated by P68 shows no clear trend in protein content at 35 days after flowering through 75 days, suggesting the physiological make-up of the seed is basically complete at the early harvest date of 36 days after pollination.

A comparison of moisture over the course of 35 days (August 17 to September 21) illustrates the rate of dry down.

The moisture data indicate there was a slightly lower grain moisture in the grain arising on the self-pollinated ears of fertile hybrid 2020 (column one) to grain resulting from the pollination of male sterile hybrid 2020-Sdms by P68 (column four). However, the rate of dry down of grain arising on self-pollinated P68 (column five) was substantially slower than the rate of dry down of grain from the self-pollinated hybrid (columns one and two) or the hybrid pollinated by P68 (columns three and four).

TABLE 4

Percent Oil, Protein and Moisture of Grain at Harvest Across Days Commencing 36 Days After Pollination Through 71 Days After Pollination of Five Corn Types (1998)

| Type(s) Planted--> | | (1) Pfister 2020 | | | (2) Pfister 2020-Sdms (Sib) | | | (3) Pfister 2020 and P68 | | | (4) Pfister 2020-Sdms and P68 | | | (5) P68 | | | GDD from Flowering to Harvest |
|---|---|---|---|---|---|---|---|---|---|---|---|---|---|---|---|---|---|
| (A) | (B) | Oil | Protein | Moist | Oil | Protein | Moist | Oil | Protein | Moist | Oil | Protein | Moist | Oil | Protein | Moist | |
| 8/17 | (36) | 4.4 | 9.9 | 47.6 | 4.0 | 10.1 | 48.3 | 8.2 | 10.3 | 51.0 | 8.4 | 12.7 | 51.6 | 16.2 | 13.6 | 50.3 | 761.5 |
| 8/21 | (40) | 4.2 | 9.6 | 45.5 | 4.3 | 9.5 | 41.8 | 8.4 | 10.3 | 45.9 | 8.9 | 10.6 | 48.5 | 18.2 | 14.6 | 44.9 | 844.0 |
| 8/26 | (45) | 4.7 | 8.9 | 37.0 | 4.3 | 8.3 | 35.3 | 8.2 | 11.6 | 40.9 | 8.8 | 9.3 | 42.3 | 16.2 | 12.2 | 38.2 | 973.0 |
| 8/31 | (50) | 3.8 | 9.8 | 30.7 | 3.9 | 12.6 | 32.4 | 8.1 | 11.7 | 32.8 | 7.0 | 13.1 | 37.0 | 13.8 | 12.6 | 34.1 | 1076.0 |
| 9/4 | (54) | 4.0 | 10.9 | 28.9* | 4.2 | 9.8 | 25.4* | 8.0 | 10.8 | 32.3* | 8.6 | 9.9 | 32.6* | 16.9 | 14.2 | 28.7* | 1156.0 |
| 9/10 | (60) | 4.3 | 10.7 | 22.9 | 4.3 | 9.8 | 22.7 | 7.8 | 11.1 | 23.0 | 8.1 | 11.2 | 24.7 | 16.0 | 13.2 | 27.8 | 1265.5 |
| 9/15 | (65) | 4.1 | 10.2 | 19.5 | 4.1 | 9.2 | 19.7 | 8.1 | 11.1 | 19.7 | 8.3 | 9.1 | 19.1 | 14.8 | 13.4 | 26.6 | 1364.0 |
| 9/17 | (67) | | | | | | | | | | | | | | | 25.4 | 1403.0 |
| 9/21 | (71) | 4.1 | 11.4 | 14.5 | 4.1 | 11.3 | 13.4 | 7.8 | 11.3 | 17.3 | 8.8 | 10.6 | 18.2 | 17.4 | 12.8 | 23.0 | 1489.0 |
| MEAN | | 4.2 | 10.2 | 30.8 | 4.1 | 10.1 | 29.9 | 8.1 | 11.0 | 32.9 | 8.4 | 10.8 | 34.2 | 16.2 | 13.3 | 33.2 | 1148.0 |

(A) = Harvest Date
(B) = Days After Pollination
*Date of black layer, physiological maturity.

Deposit Information

Applicant has made available to the public without restriction a deposit of at least 2500 seeds of synthetic hybrid P68 with the American Type Culture Collection (ATCC), Manassas, Va. 20110. The seed deposited with the ATCC was taken from the same deposit maintained by Optimum Quality Grains, L.L.C., Box 19, 90 North Fayette Street, El Paso, Ill. 61738, since prior to the filing date of this application. The deposit will be maintained in the ATCC depository, which is a public depository, for a period of 30 years, or 5 years after the most recent request, or for the effective life of the patent, whichever is longer, and will be replaced if they become nonviable during that period.

Synthetic parental seed stocks of P41.1B-Lancaster and P58.1wx-Reid have also been made available to the public without restriction from a deposit of at least 2500 seeds of each synthetic population with the ATCC under Deposit No. 209029 for P41.1B and No. 97868 for P58.1wx.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. Synthetic corn hybrid P68 having Patent Deposit Designation No. PTA-1337.

2. A synthetic corn hybrid corn seed designated P68, a representative sample of which has been deposited with the ATCC under Patent Deposit Designation PTA-1337.

3. A synthetic hybrid corn plant produced by the seed of claim 2.

4. Pollen of the synthetic hybrid corn plant of claim 3.

5. A tissue culture comprising regenerable cells of the synthetic hybrid corn plant of claim 3.

6. A corn plant regenerated from the regenerable cells of claim 5.

7. A synthetic hybrid corn plant having all the phenotypic characteristics of the synthetic hybrid corn plant of claim 3.

8. A synthetic hybrid corn plant having substantially all the phenotypic, genotypic and physiological characteristics of the hybrid corn plant of claim 3.

9. A method for producing a synthetic hybrid corn seed comprising the steps of:

a) planting in pollinating proximity seeds of corn synthetic lines P41.1B, ATCC Deposit No. 209209, and P58.1wx, ATCC Deposit No. 97868;

b) cultivating corn plants resulting from the planting until the time of flowering;

c) emasculating the flowers of the plants of either synthetic line P41.1B or P58.1wx;

d) allowing cross pollination to occur between the synthetic lines; and e) harvesting seeds produced on the emasculated plants.

10. Grain produced by crossing a synthetic hybrid corn plant according to claim 3 with another, different corn plant.

11. Seed produced by crossing a synthetic hybrid corn plant according to claim 3 with another, different corn plant.

12. A seed corn blend comprising a mixture of male sterile hybrid corn seed and the synthetic hybrid corn seed of claim 2.

13. Corn grain produced by the process of:

(a) planting, in pollinating proximity, seeds of synthetic hybrid corn plant P68, Patent Deposit Designating PTA-1337, and seeds of a male sterile corn hybrid;

(b) cultivating corn plants resulting from the planting;

(c) allowing the P68 corn plants to pollinate the male sterile hybrid corn plants; and (d) harvesting the resulting corn grain from all plants.

14. A corn plant produced from a seed of claim 2 and having the ability to impart desirable grain quality traits to a first generation grain when used as a pollinator in the TOPCROSS® Grain Production System.

15. A corn plant produced from a seed of claim 2 and having the ability to impart a high oil level to a first generation grain when used as a pollinator in the TOPCROSS® Grain Production System.

* * * * *